(12) United States Patent
Maekawa et al.

(10) Patent No.: US 9,481,694 B2
(45) Date of Patent: Nov. 1, 2016

(54) SOLID SOLUTION PIGMENT NANOPARTICLES AND METHOD FOR PRODUCING SOLID SOLUTION PIGMENT NANOPARTICLES HAVING CONTROLLED SOLID SOLUTION RATIO

(75) Inventors: Masaki Maekawa, Izumi (JP); Kaeko Araki, Izumi (JP); Hideyuki Oka, Izumi (JP); Daisuke Honda, Izumi (JP); Masakazu Enomura, Izumi (JP)

(73) Assignee: M. TECHNIQUE CO., LTD., Izumi-Shi (JP)

( * ) Notice: Subject to any disclaimer, the term of this patent is extended or adjusted under 35 U.S.C. 154(b) by 633 days.

(21) Appl. No.: 13/883,692

(22) PCT Filed: May 20, 2011

(86) PCT No.: PCT/JP2011/061692
§ 371 (c)(1),
(2), (4) Date: May 6, 2013

(87) PCT Pub. No.: WO2012/070263
PCT Pub. Date: May 31, 2012

(65) Prior Publication Data
US 2013/0220180 A1 Aug. 29, 2013

(30) Foreign Application Priority Data
Nov. 24, 2010 (JP) .................. 2010-261863

(51) Int. Cl.
| | | |
|---|---|---|
| *B01D 11/02* | (2006.01) | |
| *B01F 3/08* | (2006.01) | |
| *B01F 3/22* | (2006.01) | |
| *B29B 7/38* | (2006.01) | |
| *C09B 67/02* | (2006.01) | |
| *C09C 1/62* | (2006.01) | |
| *C07F 3/06* | (2006.01) | |
| *C09B 67/14* | (2006.01) | |
| *C09B 67/22* | (2006.01) | |
| *C09C 1/00* | (2006.01) | |
| *C09C 1/04* | (2006.01) | |
| *C07F 1/08* | (2006.01) | |
| *B82Y 30/00* | (2011.01) | |
| *C09B 67/42* | (2006.01) | |
| *C09B 67/16* | (2006.01) | |
| *C09B 67/50* | (2006.01) | |

(52) U.S. Cl.
CPC ............. *C07F 3/06* (2013.01); *B01D 11/0269* (2013.01); *B01F 3/0861* (2013.01); *B82Y 30/00* (2013.01); *C07F 1/08* (2013.01); *C09B 67/0017* (2013.01); *C09B 67/0019* (2013.01); *C09B 67/0026* (2013.01); *C09B 67/0035* (2013.01); *C09B 67/0092* (2013.01); *C09C 1/0081* (2013.01); *C09C 1/04* (2013.01); *C09C 1/627* (2013.01); *C01P 2004/64* (2013.01); *C01P 2004/82* (2013.01)

(58) Field of Classification Search
CPC ... B01D 11/00; B01D 11/02; B01D 11/0269; B01D 11/0276; B01D 11/028; B01D 11/0288; B01D 11/0476; B01D 11/048; B01D 11/04; B01D 9/00; C01G 9/02; C01G 9/003; C01G 3/003; C01G 3/02; C01G 31/003; C01G 31/02; C01G 19/003; C01G 19/03; C01G 25/003; C01G 25/02; C01G 37/002; C01G 37/02; C01G 45/02; C01G 45/003; C01G 51/003; C01G 51/04; C01D 1/04; C01D 1/28; C01D 1/34; C01D 9/02; C01F 5/22; B01J 19/1887; C07F 7/10; C07F 1/08; C07F 3/06; Y10T 428/2982; B29B 7/10; B29B 7/38; B29B 7/385; B29B 9/12; B29B 2009/125; B01F 1/00; B01F 1/005; B01F 1/0038; B01F 3/08; B01F 3/0803; B01F 3/0861; B01F 3/0865; B01F 3/22; B01F 3/223; B01F 9/00; B01F 9/0032; C09B 67/02; C09B 67/10; C09B 67/20; C09B 67/0014; C09B 67/0016; C09B 67/0017; C09B 67/0034; C09B 67/0035; C09B 67/0092; C09B 67/0019; C09B 67/0026; C09B 67/006; C09B 67/0063; C09B 67/0064; C09B 67/0065; C09B 67/0066; C09B 67/0067; C09B 67/0069;
C09B 67/007; C09C 1/04; C09C 1/62;
C09C 1/627; C09C 1/0081; C09C 3/04;
C09C 3/045; C01P 2004/62; C01P 2004/64;
C01P 2004/82; B82Y 30/00
USPC .............. 210/634, 639, 644, 787; 423/594.4,
423/594.5; 428/402; 556/31; 977/773, 810,
977/811; 264/5, 8, 11; 366/145, 187, 220,
366/152.1, 152.2, 160.1, 162.1; 106/400,
106/411, 419
See application file for complete search history.

(56) References Cited

U.S. PATENT DOCUMENTS

| | | | |
|---|---|---|---|
| 6,362,885 B1* | 3/2002 | Osumi | G01J 3/46 356/402 |
| 6,485,658 B1 | 11/2002 | Horiuchi et al. | |
| 8,133,312 B2 | 3/2012 | Saito et al. | |
| 8,183,299 B2* | 5/2012 | Enomura | 516/78 |
| 8,609,035 B2* | 12/2013 | Enomura | 422/225 |
| 8,636,974 B2* | 1/2014 | Enomura | 423/612 |
| 8,841,352 B2* | 9/2014 | Enomura | 516/22 |
| 8,889,885 B2* | 11/2014 | Enomura | 548/453 |
| 8,911,545 B2 | 12/2014 | Enomura | |
| 8,978,702 B2* | 3/2015 | Enomura | 137/896 |
| 2002/0036950 A1* | 3/2002 | Cosman et al. | 366/152.1 |
| 2004/0138475 A1 | 7/2004 | Hao et al. | |
| 2006/0137567 A1* | 6/2006 | Yadav | 106/31.9 |
| 2007/0144399 A1* | 6/2007 | Nagashima | C09B 67/0002 106/31.6 |
| 2008/0210902 A1* | 9/2008 | Coy et al. | 252/182.33 |
| 2008/0311291 A1* | 12/2008 | Schumacher et al. | 427/215 |
| 2009/0069473 A1* | 3/2009 | Kusano et al. | 524/155 |
| 2009/0117349 A1* | 5/2009 | Saito et al. | 428/195.1 |
| 2009/0241800 A1* | 10/2009 | Kyota | 106/31.85 |
| 2010/0155310 A1* | 6/2010 | Enomura | B01F 3/0807 209/668 |
| 2010/0202960 A1 | 8/2010 | Enomura | |
| 2010/0261103 A1* | 10/2010 | Sasaki et al. | 430/7 |
| 2010/0326321 A1 | 12/2010 | Enomura | |
| 2010/0327236 A1 | 12/2010 | Enomura | |
| 2011/0177337 A1 | 7/2011 | Enomura | |

FOREIGN PATENT DOCUMENTS

| | | |
|---|---|---|
| CN | 101193696 A | 6/2008 |
| CN | 101376750 A | 3/2009 |
| CN | 101795772 A | 8/2010 |
| DE | 100 20 779 A1 | 12/2000 |
| EP | 2 055 752 A2 | 5/2009 |
| EP | 2 180 021 A1 | 4/2010 |
| EP | 2 204 351 A1 | 7/2010 |
| JP | 5-72773 A | 3/1993 |
| JP | 2001-89682 A | 4/2001 |
| JP | 2003-3088 A | 1/2003 |
| JP | 2004-160309 * | 6/2004 |
| JP | 2004-250277 A | 9/2004 |
| JP | 2004-528457 A | 9/2004 |
| JP | 2005-275052 A | 10/2005 |
| JP | 2008-201914 A | 9/2008 |
| JP | 2008-231415 A | 10/2008 |
| JP | 2009-74071 A | 4/2009 |
| JP | 2009-91551 A | 4/2009 |
| JP | 4335968 B2 | 9/2009 |
| JP | 2009-251481 A | 10/2009 |
| JP | 2010-180386 A | 8/2010 |
| WO | 02/092699 A2 | 11/2002 |
| WO | WO 2006/121016 A1 | 11/2006 |
| WO | WO 2009/008388 A1 | 1/2009 |
| WO | WO 2009/008390 A1 | 1/2009 |
| WO | WO 2009/008393 * | 1/2009 |
| WO | WO 2010/035861 A1 | 4/2010 |
| WO | WO 2010/061830 A1 | 6/2010 |

OTHER PUBLICATIONS

Complete English Translation of JP 2004-160309 which was published on Jun. 2004, obtained from prosecution history of U.S. Appl. No. 12/677,606.*

* cited by examiner

*Primary Examiner* — Joseph Drodge

(74) *Attorney, Agent, or Firm* — Birch, Stewart, Kolasch & Birch, LLP

(57) ABSTRACT

The problem addressed by the present invention is to provide; solid solution pigment nanoparticles having a homogeneous solid solution ratio; a method for producing solid solution pigment nanoparticles having a homogeneous solid solution ratio in each primary particle; and a method for controlling the solid solution ratio of solid solution pigment nanoparticles. The solid solution pigment nanoparticles are prepared by precipitating at least two types of pigment by mixing a pigment precipitation solvent and; at least one type of pigment solution wherein at least two types of pigment are dissolved in a solvent: or at least two types of pigment solution wherein at least one type of pigment is dissolved in a solvent. The solid solution pigment nanoparticles are wherein the solid solution ratio of the at least two types of pigment in the primary particles of the precipitated solid solution pigment nanoparticles with respect to the ratio of the at least two types of pigment in the pigment solution mixed with the pigment precipitation solvent having a precision within 25%.

21 Claims, 6 Drawing Sheets

(A)

(B)

(A)

(B)

SOLID SOLUTION PIGMENT NANOPARTICLES AND METHOD FOR PRODUCING SOLID SOLUTION PIGMENT NANOPARTICLES HAVING CONTROLLED SOLID SOLUTION RATIO

TECHNICAL FIELD

The present invention relates to solid solution pigment nanoparticles and a method for producing solid solution pigment nanoparticles having controlled solid solution ratio.

BACKGROUND ART

It is said that, if a pigment having higher durability in weather resistance, light resistance, water resistance, heat resistance, and so on as compared with a dye is made a nanoparticle, a color material having not only the same level of color characteristics as a dye in a tinting power, a coloring power, clearness, transparency, and gloss, but also excellent durability can be produced.

When a pigment nanoparticle is used in an ink jet ink, a color filter, a printing ink, a paint, or as a colorant for tonner and plastics, it is usually used by dispersing it in water or an organic solvent. To confer an intended color tone to a colored substance by using a pigment, a toning method in which pigments having different color tones are mixed is generally used. However, in many cases, a plurality of pigments which are used in this toning method have different chemical properties so that it is difficult to obtain a stable dispersion state; and thus, an advanced technology, high cost, and high energy are required to disperse a plurality of pigments stably.

To solve the problem as mentioned above, a toning method in which two or more types of pigment are made to a solid solution in a single particle has been known. As to the method to make a solid solution of pigments, there are several methods such as: a method in which a mixture of two or more types of pigment is subjected to a crushing treatment or a heat treatment as shown in Patent Document 1; a method in which a mixed pigment solution obtained by dissolving two or more types of pigment into a solvent is poured into an aqueous solvent as shown in Patent Document 2; and a method in which two or more pigment solutions having two or more types of pigment dissolved in each good solvent for respective pigments are simultaneously or sequentially mixed with one solvent capable of becoming a poor solvent to any of these solutions as shown in Patent Document 3.

However, in any of these methods, to produce a solid solution pigment nanoparticle having not only a uniform and fine particle diameter but also a uniform solid solution ratio in each particle has been very difficult. In the intended toning, a solid solution pigment nanoparticle having a uniform solid solution ratio in each nanoparticle has been wanted; and in addition, a method for producing a solid solution pigment nanoparticle having a controlled solid solution ratio has been eagerly wanted.

Applicant of the present invention provided, as shown in Patent Document 4, a method to produce a pigment nanoparticle wherein pigment particles are separated in a thin film fluid that flows between processing surfaces which are disposed in a position they are faced with each other; but a specific method for producing a solid solution pigment nanoparticle having a uniformly controlled solid solution ratio has not been disclosed.

Patent Document 1: Japanese Patent Application Publication No. 2004-528457
Patent Document 2: Japanese Patent Laid-Open Publication No. 2008-201914
Patent Document 3: Japanese Patent Laid-Open Publication No. 2009-74071
Patent Document 4: International Patent Laid-Open Publication No. 2009/008388

DISCLOSURE OF THE INVENTION

Problems to be Solved by the Invention

The present invention is to solve the problems mentioned above and its object is to provide a solid solution pigment nanoparticle having a uniform solid solution ratio. In addition, the present invention provides a method for producing a solid solution pigment nanoparticle having a uniform solid solution ratio in each primary particle thereof, and a method for controlling a solid solution ratio of a solid solution pigment nanoparticle.

Means for Solving the Problems

Inventors of the present invention carried out extensive investigation, and as a result, it was found that, in separation of pigment nanoparticles by mixing a pigment solution having a pigment dissolved in a solvent with a pigment separation solvent, uniform and homogeneous solid solution pigment nanoparticles can be obtained by separating two or more types of pigment between at least two processing surfaces which are disposed in a position they are faced with each other so as to be able to approach to and separate from each other, at least one of which rotates relative to the other. In addition, it was found that a solid solution ratio in a solid solution pigment nanoparticle can be controlled by controlling a ratio of two or more types of pigment in a pigment solution to be mixed in a thin film fluid formed between the at least two processing surfaces.

An invention according to claim 1 of the present application provides a solid solution pigment nanoparticle, wherein the said solid solution pigment nanoparticle is a solid solution pigment nanoparticle that is produced by separating at least two types of pigment by mixing a pigment separation solvent with at least one pigment solution having at least two types of pigment dissolved in a solvent or at least two pigment solutions having at least one type of pigment dissolved in a solvent, wherein a solid solution ratio of at least two types of pigment in a primary particle of the separated solid solution pigment nanoparticles relative to a ratio of at least two types of pigment in the pigment solution mixed with the pigment separation solvent is within 25% as a degree of precision.

An invention according to claim 2 of the present application provides a solid solution pigment nanoparticle, wherein the said solid solution pigment nanoparticle is a solid solution pigment nanoparticle that is produced by separating at least two types of pigment by mixing a pigment separation solvent with at least one pigment solution having at least two types of pigment dissolved in a solvent or at least two pigment solutions having at least one type of pigment dissolved in a solvent, wherein a solid solution ratio of at least two types of pigment in a primary particle of the separated solid solution pigment nanoparticles relative to a ratio of at least two types of pigment in the pigment solution mixed with the pigment separation solvent is within 10% as a degree of precision.

An invention according to claim 3 of the present application provides a solid solution pigment nanoparticle, wherein the said solid solution pigment nanoparticle is a solid solution pigment nanoparticle that is produced by separating at least two types of pigment by mixing a pigment separation solvent with at least one pigment solution having at least two types of pigment dissolved in a solvent or at least two pigment solutions having at least one type of pigment dissolved in a solvent, wherein a solid solution ratio of at least two types of pigment in a primary particle of the separated solid solution pigment nanoparticles relative to a ratio of at least two types of pigment in the pigment solution mixed with the pigment separation solvent is within 5% as a degree of precision.

An invention according to claim 4 of the present application provides the solid solution pigment nanoparticle according to any one of claims 1 to 3, wherein the degree of precision of the solid solution ratio of at least two types of pigment in a primary particle of the separated solid solution pigment nanoparticles relative to the ratio of at least two types of pigment in the pigment solution mixed with the pigment separation solvent is obtained by a TEM-EDS measurement with the observation condition of 250,000 or more magnification.

An invention according to claim 5 of the present application provides the solid solution pigment nanoparticle according to any one of claims 1 to 3, wherein the degree of precision of the solid solution ratio obtained by the TEM-EDS measurement relative to the solid solution ratio obtained by an ICP emission spectrometric analysis of the solid solution pigment nanoparticle is within 20%.

An invention according to claim 6 of the present application provides a method for producing the solid solution pigment nanoparticle according to any one of claims 1 to 3, wherein at least two fluids are used as a fluid to be processed, of these at least one fluid is a pigment solution having at least two types of pigment dissolved in a solvent, and at least one fluid other than the said fluid is a pigment separation solvent to separate the pigments, wherein the two fluids to be processed are mixed in a thin film fluid formed between at least two processing surfaces which are disposed in a position they are faced with each other so as to be able to approach to and separate from each other, at least one of which rotates relative to the other, thereby separating the solid solution pigment nanoparticle having a controlled solid solution ratio.

An invention according to claim 7 of the present application provides the method for producing the solid solution pigment nanoparticle according to any one of claims 1 to 3, wherein at least three fluids of a first, a second, and a third fluids are used as fluids to be processed, wherein the first fluid is a first pigment solution having at least one type of pigment dissolved in a solvent, the second fluid is a second pigment solution having at least one type of pigment dissolved in a solvent, the said pigment being different from the pigment dissolved in the first pigment solution, and the third fluid is a pigment separation solvent to separate the pigments, wherein the first pigment solution and the second pigment solution are used as a pigment solution, and the three fluids to be processed are mixed in a thin film fluid formed between at least two processing surfaces which are disposed in a position they are faced with each other so as to be able to approach to and separate from each other, at least one of which rotates relative to the other, thereby separating the solid solution pigment nanoparticle having a controlled solid solution ratio.

An invention according to claim 8 of the present application provides the method for producing a solid solution pigment nanoparticle according to claim 6 or 7, wherein a solid solution ratio of at least two different types of pigment in the solid solution pigment nanoparticle is controlled by controlling a ratio of at least two different types of pigment in the pigment solution to be mixed in the thin film fluid.

An invention according to claim 9 of the present application provides the method for producing a solid solution pigment nanoparticle according to claim 8, wherein the ratio of the pigments is a mixture dissolution ratio (mol ratio).

Advantages

According to the present invention, a solid solution pigment nanoparticle having a uniform solid solution ratio could be provided by separating the pigment nanoparticle by mixing a pigment solution having a pigment dissolved in a solvent with a pigment separation solvent, wherein two or more types of pigment are separated by this mixing in a thin film formed between at least two processing surfaces which are disposed in a position they are faced with each other so as to be able to approach to and separate from each other, at least one of which rotates relative to the other. In addition, a method for producing the solid solution pigment nanoparticle having a uniform solid solution ratio in each primary particle of the solid solution pigment nanoparticle and a method for controlling a solid solution ratio of the solid solution pigment nanoparticle are provided.

TECHNICAL FIELD

FIG. 4

Figure 1:
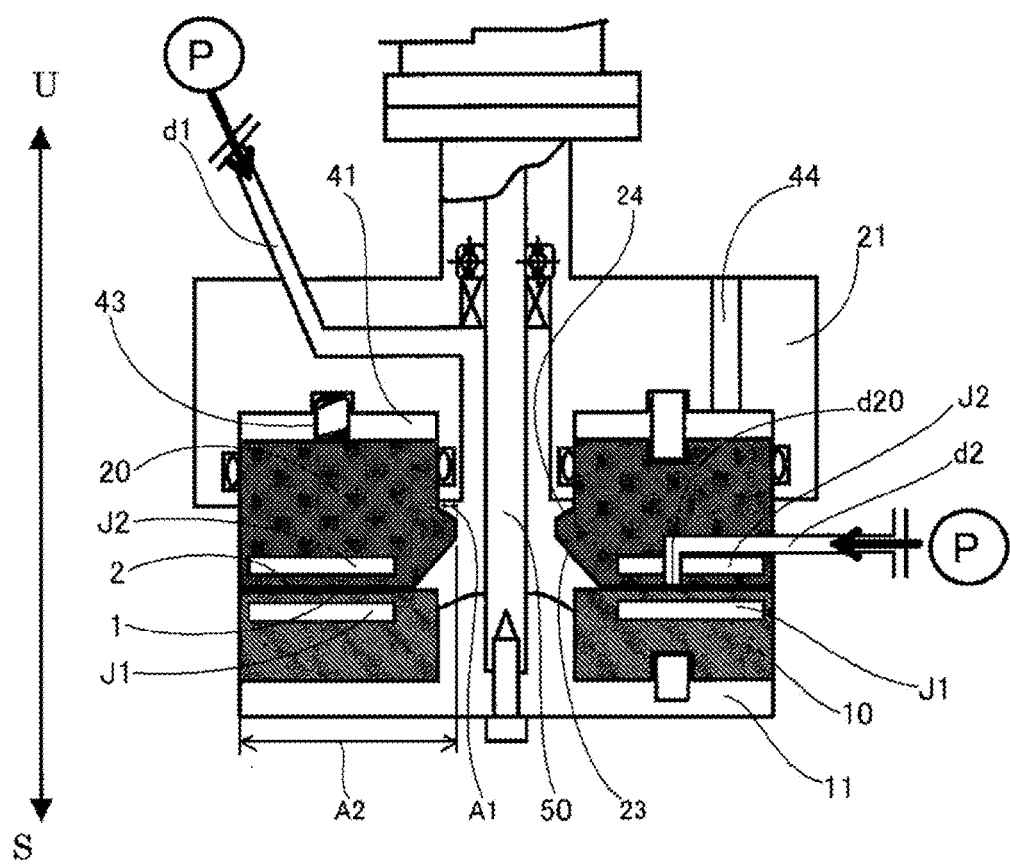
FIG. 1 is a schematic sectional view showing the fluid processing apparatus according to an embodiment of the present invention.

This shows a TEM picture of the solid solution pigment nanoparticles obtained in Example 3 of the present invention.

FIG. 5

This shows transmission spectra of dispersion solutions of the solid solution pigment nanoparticles obtained in Example 1, Example 3, and Example 5 of the present invention, as well as Comparative Example 2, in the wavelength region of 350 to 800 nm.

FIG. 6

This shows a TEM picture of the solid solution pigment nanoparticles obtained in Example 8 of the present invention.

BEST MODES FOR CARRYING OUT THE INVENTION

Hereunder, the present invention will be explained in detail. However, a technical scope of the present invention is not limited by the following embodiments and Examples.

In the present invention, in the solid solution pigment nanoparticles, which is produced by separating at least two types of pigment by mixing a pigment separation solvent with at least one pigment solution having at least two types of pigment dissolved in a solvent or at least two pigment solutions having at least one type of pigment dissolved in a solvent, a solid solution ratio of at least two types of pigment in a primary particle of the separated solid solution pigment nanoparticles relative to a ratio of at least two types of pigment in the pigment solution mixed with the pigment separation solvent is within 25%, preferably within 10%, or more preferably within 5% as a degree of precision. If the degree of precision is more than 25%, not only a color tone of each pigment nanoparticle may be different but also, because of its chemical properties, there is a possibility of giving a harmful effect to the dispersibility or to the interaction thereof with a solvent or a dispersing agent used therein.

A method to obtain the degree of precision in the solid solution ratio of a plurality of pigments in a primary particle of the separated solid solution pigment nanoparticles relative to a ratio of a plurality of pigments in the pigment solution mixed with the pigment separation solvent is not particularly restricted provided that the solid solution ratio (component ratio, concentration ratio, or mol ratio) of different types of pigment in the primary particle can be obtained; but a preferable method thereof is a TEM-EDS measurement method with an observation condition of magnification of 250,000 or more, preferably 500,000 or more, or more preferably 1,000,000 or more. In one example thereof, the degree of precision can be obtained from the solid solution ratio (component ratio, concentration ratio, or mol ratio) calculated from the EDS measurement of preferably a primary particle confirmed by a TEM observation with magnification of 250,000 or more relative to the ratio (mol ratio) of a plurality of pigments in the pigment solution mixed with the pigment separation solvent. In addition, though not restricted, a solid NMR method and the like may be mentioned as the methods other than the TEM-EDS measurement method. Further, the degree of precision of the solid solution ratio of the solid solution pigment nanoparticles obtained by the TEM-EDS measurement relative to the solid solution ratio thereof obtained by an ICP emission spectrometric analysis is within 20%, preferably within 10%, or more preferably within 5%. The ICP emission spectrometric analysis is to analyze the solid solution ratio of a solid solution pigment nanoparticle aggregate, or in other words, the solid solution ratio of the solid solution pigment nanoparticles contained in powders or a dispersion solution of the solid solution pigment nanoparticles. An illustrative example of the analysis method other than the ICP emission spectrometric analysis includes a thermal analysis such as TG-DTA and DSC, IR and NMR (solution), gas chromatography, liquid chromatography, ion chromatography, XPS, SIMS, and TOF-SIMS.

Although the pigment in the present invention is not particularly restricted, illustrative example thereof includes an organic pigment, an inorganic pigment, an organic inorganic composite pigment, and all pigments registered in The Society of Dyers and Colorists.

Although the organic pigment in the present invention is not particularly restricted, an illustrative example thereof includes a perylene compound pigment, a perynone compound pigment, a quinacridone compound pigment, a quinacridone compound quinone pigment, an anthraquinone compound pigment, an anthanthrone compound pigment, a benzimidazolone compound pigment, a disazo condensate compound pigment, a disazo compound pigment, an azo compound pigment, an indanthrone compound pigment, a phthalocyanine compound pigment, a triaryl carbonium compound pigment, a dioxazine compound pigment, an aminoanthraquinone compound pigment, a diketo pyrrolopyrrole compound pigment, a thioindigo compound pigment, an isoindoline compound pigment, an isoindolinone compound pigment, a pyranthrone compound pigment, and an isoviolanthrone compound pigment, or a mixture of them.

Although the inorganic pigment in the present invention is not particularly restricted, an illustrative example thereof includes a metal compound. An illustrative example thereof includes a red iron oxide, a black iron oxide, a yellow iron oxide, a white pigment such as titanium oxide and zinc oxide, Prussian blue, ultramarine blue, chromium oxide, magnesium oxide, aluminum oxide, calcium oxide, zirconium oxide, cadmium sulfide, zinc sulfide, other inorganic color pigment, and every metal compound such as general inorganic compounds.

The foregoing pigments may be used in the present invention. In the present invention, one pigment solution of a mixed pigment solution having two or more foregoing types of pigment dissolved in a solvent may be prepared; or a plurality of pigment solutions having two or more foregoing types of pigment dissolved in each solvent may be prepared. Alternatively, a plurality of pigment solutions may be prepared by a combination of them. On this occasion, a pigment may be dissolved in the state of molecular dispersion, or in the state of being ionized or salified.

An illustrative example of the solvent for dissolution or molecular dispersion of the foregoing pigments includes water and an organic solvent, or a mixed solvent composed of a plurality of them. An illustrative example of water includes a tap water, an ion-exchanged water, a pure water, a ultrapure water, and a RO water. An illustrative example of the organic solvent includes an alcohol compound solvent, an amide compound solvent, a ketone compound solvent, an ether compound solvent, an aromatic compound solvent, a carbon disulfide, an aliphatic compound solvent, a nitrile compound solvent, a sulfoxide compound solvent, a halogen-containing compound solvent, an ester compound solvent, an ionic liquid, a carboxylic acid compound, and a sulfonic acid compound. These solvents may be used singly or as a mixture of a plurality of them.

Alternatively, it is also possible to mix or dissolve a basic substance or an acidic substance in the foregoing solvents for use. An illustrative example of the basic substance includes a metal hydroxide such as sodium hydroxide and potassium hydroxide; a metal alkoxide such as sodium methoxide and sodium isopropoxide; and an amine compound such as triethylamine, diethylamino ethanol, and diethylamine. An illustrative example of the acidic substance includes an inorganic acid such an aqua regia, hydrochloric acid, nitric acid, fuming nitric acid, sulfuric acid, fuming sulfuric acid, and chlorosulfuric acid; and an organic acid such as formic acid, acetic acid, chloroacetic acid, dichloroacetic acid, oxalic acid, trifluoroacetic acid, trichloroacetic acid, methanesulfonic acid, and dodecylbenzene sulfonic acid. These basic substances or acidic substances may be used as a mixture with the foregoing various solvents, or each of them may be used singly.

To explain the foregoing solvents in more detail, an illustrative example of the alcohol compound solvent includes a methanol, an ethanol, an isopropanol, a n-propanol, and a 1-methoxy-2-propanol; a linear alcohol such as n-butanol; a branched alcohol such as 2-butanol and tert-butanol; a polyol such as ethylene glycol and diethylene glycol; and a propylene glycol monoethyl ether. An illustrative example of the ketone compound solvent includes an acetone, a methyl ethyl ketone, and a cyclohexanone. An illustrative example of the ether compound solvent includes a dimethyl ether, a diethyl ether, and a tetrahydrofuran. An illustrative example of the aromatic compound solvent includes a nitrobenzene, a chlorobenzene, and a dichlorobenzene. An illustrative example of the aliphatic compound solvent includes a hexane. An illustrative example of the nitrile compound solvent includes an acetonitrile. An illustrative example of the sulfoxide compound solvent includes a dimethyl sulfoxide, a diethyl sulfoxide, a hexamethylene sulfoxide, and a sulfolane. An illustrative example of the halogen-containing compound solvent includes a chloroform, a dichloromethane, a trichloroethylene, and an iodoform. An illustrative example of the ester compound solvent includes an ethyl acetate, a butyl acetate, a methyl lactate, a ethyl lactate, and a 2-(1-methox)propyl acetate. An illustrative example of the ionic liquid includes a salt of a 1-butyl-3-methylimidazolium with a PF6 (hexafluorophosphate ion). An illustrative example of the amide compound solvent includes a N,N-dimethyl formamide, a 1-methyl-2-pyrrolidone, a 2-pyrrolidinone, a 1,3-dimethyl-2-imidazolidinone, a 2-pyrrolidinone, a ϵ-caprolactam, a formamide, a N-methyl formamide, an acetamide, a N-methyl acetamide, a N,N-dimethyl acetamide, a N-methyl propane amide, and a hexamethylphosphoric triamide. An illustrative example of the carboxylic acid compound includes a 2,2-dichloropropionic acid and a squaric acid. An illustrative example of the sulfonic acid compound includes a methanesulfonic acid, a p-toluenesulfonic acid, a chlorosulfonic acid, and a trifluoromethanesulfonic acid.

As to the pigment separation solvent to separate pigments by mixing with the pigment solution, the same solvents as the foregoing solvents may be used. In accordance with types of the pigment to constitute the intended solid solution pigment nanoparticles, a solvent to dissolve and a solvent to separate may be selected for use.

In the present invention, mixing of the fluid which contains the pigment solution with the fluid which contains the pigment separation solvent is preferably done by a method in which uniform and forced stirring, mixing, and dispersing are effected in a thin film fluid formed between processing surfaces which are disposed in a position they are faced with each other so as to be able to approach to and separate from each other, at least one of which rotates relative to the other. An illustrative example of the apparatus like this includes an apparatus based on the same principle as that described in the Patent Document 4 filed by the present applicant. By using the apparatus based on the principle like this, production of uniform and homogeneous solid solution pigment nanoparticles may be possible. However, this production method is only one mere example; and thus, the present invention is not limited to this production method.

Hereunder, embodiments of the apparatus will be explained with referring to the drawings.

Figure 2:
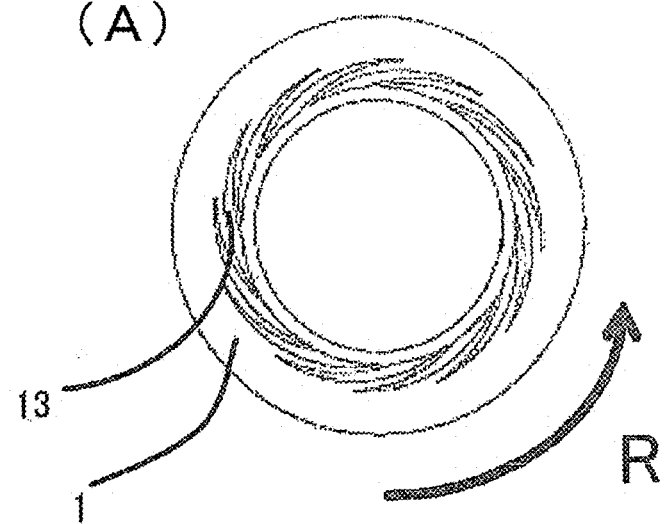
FIG. 2(A) is a schematic plane view of the first processing surface in the fluid processing apparatus shown in FIG. 1.
FIG. 2(B) is an enlarged view showing an important part of the processing surface in the apparatus.
Figure 2:
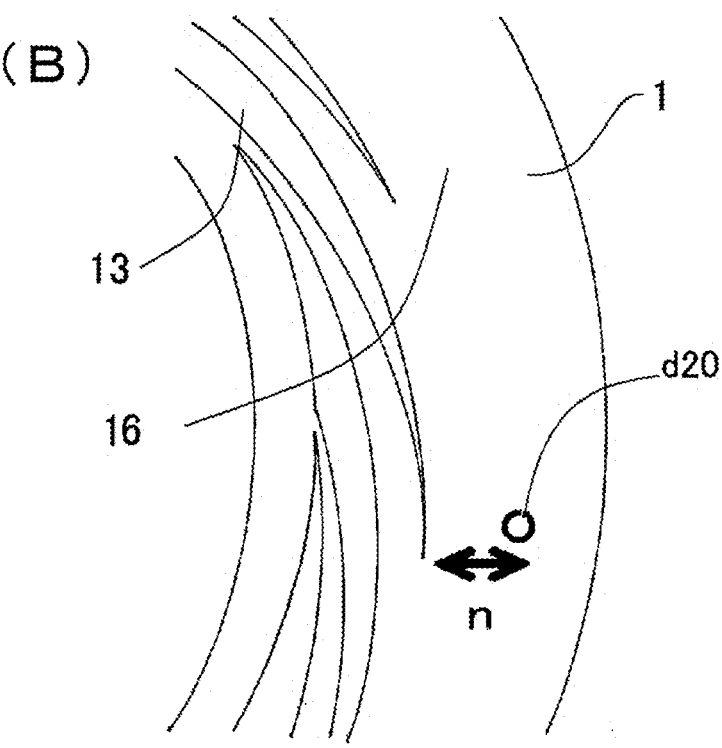
Figure 3:
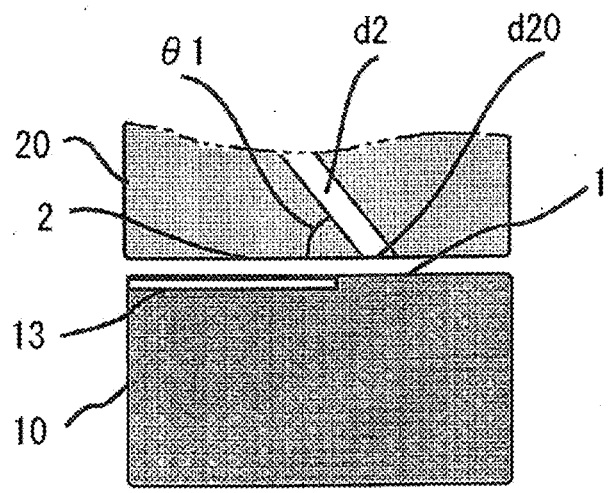
FIG. 3(A) is a sectional view of the second introduction part of the apparatus.
FIG. 3(B) is an enlarged view showing an important part of the processing surface for explaining the second introduction part.
Figure 3:
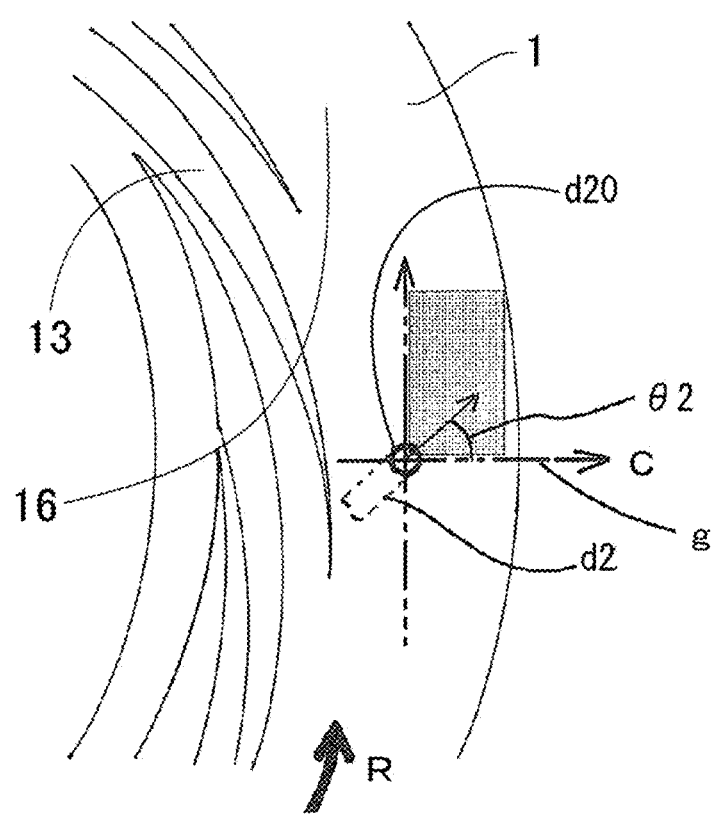

The fluid processing apparatus shown in FIG. 1 to FIG. 3 is similar to the apparatus described in Patent Document 4, with which a material to be processed is processed between processing surfaces in processing members arranged so as to be able to approach to and separate from each other, at least one of which rotates relative to the other; wherein, of the fluids to be processed, a first fluid to be processed, i.e., a first fluid, is introduced into between the processing surfaces, and a second fluid to be processed, i.e., a second fluid, is introduced into between the processing surfaces from a separate path that is independent of the flow path introducing the afore-mentioned first fluid and has an opening leading to between the processing surfaces, whereby the first fluid and the second fluid are mixed and stirred between the processing surfaces. Meanwhile, in FIG. 1, a reference character U indicates an upside and a reference character S indicates a downside; however, up and down, front and back and right and left shown therein indicate merely a relative positional relationship and does not indicate an absolute position. In FIG. 2(A) and FIG. 3(B), reference character R indicates a rotational direction. In FIG. 3(C), reference character C indicates a direction of centrifugal force (a radial direction).

In this apparatus provided with processing surfaces arranged opposite to each other so as to be able to approach to and separate from each other, at least one of which rotates relative to the other, at least two kinds of fluids to be processed are used as the fluid to be processed, wherein at least one fluid thereof contains at least one kind of material to be processed, a thin film fluid is formed by converging the respective fluids between these processing surfaces, and the material to be processed is processed in this thin film fluid. With this apparatus, a plurality of fluids to be processed may be processed as mentioned above; but a single fluid to be processed may be processed as well.

This fluid processing apparatus is provided with two processing members of a first processing member 10 and a second processing member 20 arranged opposite to each other, wherein at least one of these processing members rotates. The surfaces arranged opposite to each other of the respective processing members 10 and 20 are made to be the respective processing surfaces. The first processing member 10 is provided with a first processing surface 1 and the second processing member 20 is provided with a second processing surface 2.

The processing surfaces 1 and 2 are connected to a flow path of the fluid to be processed and constitute part of the flow path of the fluid to be processed. Distance between these processing surfaces 1 and 2 can be changed as appropriate; and thus, the distance thereof is controlled so as to form a minute space usually less than 1 mm, for example, in the range of about 0.1 µm to about 50 µm. With this, the fluid to be processed passing through between the processing surfaces 1 and 2 becomes a forced thin film fluid forced by the processing surfaces 1 and 2.

When a plurality of fluids to be processed are processed by using this apparatus, the apparatus is connected to a flow path of the first fluid to be processed whereby forming part of the flow path of the first fluid to be processed; and part of the flow path of the second fluid to be processed other than the first fluid to be processed is formed. In this apparatus, the two paths converge into one, and two fluids to be processed are mixed between the processing surfaces 1 and 2 so that the fluids may be processed by reaction and so on. It is noted here that the term "process(ing)" includes not only the embodiment wherein a material to be processed is reacted but also the embodiment wherein a material to be processed is only mixed or dispersed without accompanying reaction.

To specifically explain, this apparatus is provided with a first holder 11 for holding the first processing member 10, a second holder 21 for holding the second processing member 20, a surface-approaching pressure imparting mechanism, a rotation drive mechanism, a first introduction part d1, a second introduction part d2, and a fluid pressure imparting mechanism p.

As shown in FIG. 2(A), in this embodiment, the first processing member 10 is a circular body, or more specifically a disk with a ring form. Similarly, the second processing member 20 is a disk with a ring form. A material of the processing members 10 and 20 is not only metal but also carbon, ceramics, sintered metal, abrasion-resistant steel, sapphire, other metal subjected to hardening treatment, and rigid material subjected to lining, coating, or plating. In the processing members 10 and 20 of this embodiment, at least part of the first and the second surfaces 1 and 2 arranged opposite to each other is mirror-polished.

Roughness of this mirror polished surface is not particularly limited; but surface roughness Ra is preferably 0.01 µm to 1.0 µm, or more preferably 0.03 µm to 0.3 µm.

At least one of the holders can rotate relative to the other holder by a rotation drive mechanism such as an electric motor (not shown in drawings). A reference numeral 50 in FIG. 1 indicates a rotary shaft of the rotation drive mechanism; in this embodiment, the first holder 11 attached to this rotary shaft 50 rotates, and thereby the first processing member 10 attached to this first holder 11 rotates relative to the second processing member 20. As a matter of course, the second processing member 20 may be made to rotate, or the both may be made to rotate. Further in this embodiment, the first and second holders 11 and 21 may be fixed, while the first and second processing members 10 and 20 may be made to rotate relative to the first and second holders 11 and 21.

At least any one of the first processing member 10 and the second processing member 20 is able to approach to and separate from at least any other member, thereby the processing surfaces 1 and 2 are able to approach to and separate from each other.

In this embodiment, the second processing member 20 approaches to and separates from the first processing member 10, wherein the second processing member 20 is accepted in an accepting part 41 arranged in the second holder 21 so as to be able to rise and set. However, as opposed to the above, the first processing member 10 may approach to and separate from the second processing member 20, or both of the processing members 10 and 20 may approach to and separate from each other.

This accepting part 41 is a concave portion for mainly accepting that side of the second processing member 20 opposite to the second processing surface 2, and this concave portion is a groove being formed into a circle, i.e., a ring when viewed in a plane. This accepting part 41 accepts the second processing member 20 with sufficient clearance so that the second processing member 20 may rotate. Meanwhile, the second processing member 20 may be arranged so as to be movable only parallel to the axial direction; alternatively, the second processing member 20 may be made movable, by making this clearance larger, relative to the accepting part 41 so as to make the center line of the processing member 20 inclined, namely unparallel, to the axial direction of the accepting part 41, or movable so as to deviate the center line of the processing member 20 and the center line of the accepting part 41 toward the radical direction.

It is preferable that the second processing member 20 be accepted by a floating mechanism so as to be movable in the three dimensional direction, as described above.

The fluids to be processed are introduced into between the processing surfaces 1 and 2 from the first introduction part d1 and the second introduction part d2 under the state that pressure is applied thereto by a fluid pressure imparting mechanism p consisting of various pumps, potential energy, and so on. In this embodiment, the first introduction part d1 is a flow path arranged in the center of the circular second holder 21, and one end thereof is introduced into between the processing surfaces 1 and 2 from inside the circular processing members 10 and 20. Through the second introduction part d2, the second fluid to be processed for reaction to the first fluid to be processed is introduced into between the processing surfaces 1 and 2. In this embodiment, the second introduction part d2 is a flow path arranged inside the second processing member 20, and one end thereof is open at the second processing surface 2. The first fluid to be processed which is pressurized with the fluid pressure imparting mechanism p is introduced from the first introduction part d1 to the space inside the processing members 10 and 20 so as to pass through between the first and second processing surfaces 1 and 2 to outside the processing members 10 and 20. From the second introduction part d2, the second fluid to be processed which is pressurized with the fluid pressure imparting mechanism p is provided into between the processing surfaces 1 and 2, whereat this fluid is converged with the first fluid to be processed, and there, various fluid processing such as mixing, stirring, emulsification, dispersion, reaction, deposition, crystallization, and separation are effected, and then the fluid thus processed is discharged from the processing surfaces 1 and 2 to outside the processing members 10 and 20. Meanwhile, an environment outside the processing members 10 and 20 may be made negative pressure by a vacuum pump.

The surface-approaching pressure imparting mechanism mentioned above supplies the processing members with force exerting in the direction of approaching the first processing surface 1 and the second processing surface 2 each other. In this embodiment, the surface-approaching pressure imparting mechanism is arranged in the second holder 21 and biases the second processing member 20 toward the first processing member 10.

The surface-approaching pressure imparting mechanism is a mechanism to generate a force (hereinafter "surface-approaching pressure") to press the first processing surface 1 of the first processing member 10 and the second processing surface 2 of the second processing member 20 in the direction to make them approach to each other. By the balance between this surface-approaching pressure and the force to separate the processing surfaces 1 and 2 from each other, i.e., the force such as the fluid pressure, a thin film fluid having minute thickness in a level of nanometer or micrometer is generated. In other words, the distance between the processing surfaces 1 and 2 is kept in a predetermined minute distance by the balance between these forces.

In the embodiment shown in FIG. 1, the surface-approaching pressure imparting mechanism is arranged between the accepting part 41 and the second processing member 20. Specifically, the surface-approaching pressure imparting mechanism is composed of a spring 43 to bias the second processing member 20 toward the first processing member 10 and a biasing-fluid introduction part 44 to introduce a biasing fluid such as air and oil, wherein the surface-approaching pressure is provided by the spring 43 and the fluid pressure of the biasing fluid. The surface-approaching pressure may be provided by any one of this spring 43 and the fluid pressure of this biasing fluid; and other forces such as magnetic force and gravitation may also be used. The second processing member 20 recedes from the first processing member 10 thereby making a minute space between the processing surfaces by separating force, caused by viscosity and the pressure of the fluid to be processed applied by the fluid pressure imparting mechanism p, against the bias of this surface-approaching pressure imparting mechanism. By this balance between the surface-approaching pressure and the separating force as mentioned above, the first processing surface 1 and the second processing surface 2 can be set with the precision of a micrometer level; and thus the minute space between the processing surfaces 1 and 2 may be set. The separating force mentioned above includes fluid pressure and viscosity of the fluid to be processed, centrifugal force by rotation of the processing members, negative pressure when negative pressure is applied to the biasing-fluid introduction part 44, and spring force when the spring 43 works as a pulling spring. This surface-approaching pressure imparting mechanism may be arranged also in the first processing member 10, in place of the second processing member 20, or in both of the processing members.

To specifically explain the separation force, the second processing member 20 has the second processing surface 2 and a separation controlling surface 23 which is positioned inside the processing surface 2 (namely at the entering side of the fluid to be processed into between the first and second processing surfaces 1 and 2) and next to the second processing surface 2. In this embodiment, the separation controlling surface 23 is an inclined plane, but may be a horizontal plane. The pressure of the fluid to be processed acts to the separation controlling surface 23 to generate force directing to separate the second processing member 20 from the first processing member 10. Therefore, the second processing surface 2 and the separation controlling surface 23 constitute a pressure receiving surface to generate the separation force.

In the example shown in FIG. 1, an approach controlling surface 24 is formed in the second processing member 20. This approach controlling surface 24 is a plane opposite, in the axial direction, to the separation controlling surface 23 (upper plane in FIG. 1) and, by action of pressure applied to the fluid to be processed, generates force of approaching the second processing member 20 toward the first processing member 10.

Meanwhile, the pressure of the fluid to be processed exerted on the second processing surface 2 and the separation controlling surface 23, i.e., the fluid pressure, is understood as force constituting an opening force in a mechanical seal. The ratio (area ratio A1/A2) of a projected area A1 of the approach controlling surface 24 projected on a virtual plane perpendicular to the direction of approaching and separating the processing surfaces 1 and 2, that is, to the direction of rising and setting of the second processing member 20 (axial direction in FIG. 1), to a total area A2 of the projected area of the second processing surface 2 of the second processing member 20 and the separation controlling surface 23 projected on the virtual plane is called as balance ratio K, which is important for control of the opening force. This opening force can be controlled by the pressure of the fluid to be processed, i.e., the fluid pressure, by changing the balance line, i.e., by changing the area A1 of the approach controlling surface 24.

Sliding surface actual surface pressure P, i.e., the fluid pressure out of the surface-approaching pressures, is calculated according to the following equation:

$$P = P1 \times (K-k) + Ps$$

Here, P1 represents the pressure of a fluid to be processed, i.e., the fluid pressure, K represents the balance ratio, k represents an opening force coefficient, and Ps represents a spring and back pressure.

By controlling this balance line to control the sliding surface actual surface pressure P, the space between the processing surfaces 1 and 2 is formed as a desired minute space, thereby forming a fluid film of the fluid to be processed so as to make the processed substance such as a product fine and to effect uniform processing by reaction.

Meanwhile, the approach controlling surface 24 may have a larger area than the separation controlling surface 23, though this is not shown in the drawing.

The fluid to be processed becomes a forced thin film fluid by the processing surfaces 1 and 2 that keep the minute space therebetween, whereby the fluid is forced to move out from the circular, processing surfaces 1 and 2. However, the first processing member 10 is rotating; and thus, the mixed fluid to be processed does not move linearly from inside the circular, processing surfaces 1 and 2 to outside thereof, but does move spirally from the inside to the outside thereof by a resultant vector acting on the fluid to be processed, the vector being composed of a moving vector toward the radius direction of the circle and a moving vector toward the circumferential direction.

Meanwhile, a rotary shaft 50 is not only limited to be placed vertically, but may also be placed horizontally, or at a slant. This is because the fluid to be processed is processed in a minute space between the processing surfaces 1 and 2 so that the influence of gravity can be substantially eliminated. In addition, this surface-approaching pressure imparting mechanism can function as a buffer mechanism of micro-vibration and rotation alignment by concurrent use of the foregoing floating mechanism with which the second processing member 20 may be held displaceably.

In the first and second processing members 10 and 20, the temperature thereof may be controlled by cooling or heating at least any one of them; in FIG. 1, an embodiment having temperature regulating mechanisms J1 and J2 in the first and second processing members 10 and 20 is shown. Alternatively, the temperature may be regulated by cooling or heating the introducing fluid to be processed. These temperatures may be used to separate the processed substance or may be set so as to generate Benard convection or Marangoni convection in the fluid to be processed between the first and second processing surfaces 1 and 2.

As shown in FIG. 2, in the first processing surface 1 of the first processing member 10, a groove-like depression 13 extended toward an outer side from the central part of the first processing member 10, namely in a radius direction, may be formed. The depression 13 may be, as a plane view, curved or spirally extended on the first processing surface 1 as shown in FIG. 2(B), or, though not shown in the drawing, may be extended straight radially, or bent at a right angle, or jogged; and the depression may be continuous, intermittent, or branched. In addition, this depression 13 may be formed also on the second processing surface 2, or on both of the first and second processing surfaces 1 and 2. By forming the depression 13 as mentioned above, the micro-pump effect can be obtained so that the fluid to be processed may be sucked into between the first and second processing surfaces 10 and 20.

The base end of the depression 13 reaches preferably inner circumference of the first processing member 10. The front end of the depression 13 extends in an outer circumferential direction of the first processing surface 1 with the depth thereof (cross-sectional area) being gradually shallower as going from the base end toward the front end.

Between the front end of the depression 13 and the outer periphery of the first processing surface 1 is arranged a flat surface 16 not having the depression 13.

When an opening d20 of the second introduction part d2 is arranged in the second processing surface 2, the arrangement is done preferably at a position opposite to the flat surface 16 of the first processing surface 1 arranged at a position opposite thereto.

This opening d20 is arranged preferably in the downstream (outside in this case) of the depression 13 of the first processing surface 1. The opening is arranged especially preferably at a position opposite to the flat surface 16 located nearer to the outer diameter than a position where the direction of flow upon introduction by the micro-pump effect is changed to the direction of a spiral and laminar flow formed between the processing surfaces. Specifically, in FIG. 2(B), a distance n from the outermost side of the depression 13 arranged in the first processing surface 1 in the radial direction is preferably about 0.5 mm or more. Especially in the case of separating nanosized microparticles (nanoparticles) from a fluid, it is preferable that mixing of a plurality of fluids to be processed and separation of the nanoparticles therefrom be effected under the condition of a laminar flow.

This second introduction part d2 may have directionality. For example, as shown in FIG. 3(A), the direction of introduction from the opening d20 of the second processing surface 2 is inclined at a predetermined elevation angle ($\theta 1$) relative to the second processing surface 2. The elevation angle ($\theta 1$) is set at more than 0° and less than 90°, and when the reaction speed is high, the angle ($\theta 1$) is preferably set in the range of 1° to 45°.

In addition, as shown in FIG. 3(B), introduction from the opening d20 of the second processing surface 2 has directionality in a plane along the second processing surface 2. The direction of introduction of this second fluid is in the outward direction departing from the center in a radial component of the processing surface and in the forward direction in a rotation component of the fluid between the rotating processing surfaces. In other words, a predetermined angle ($\theta 2$) exists facing the rotation direction R from a reference line g, which is the line to the outward direction and in the radial direction passing through the opening d20. This angle ($\theta 2$) is also set preferably at more than 0° and less than 90°.

This angle ($\theta 2$) can vary depending on various conditions such as the type of fluid, the reaction speed, viscosity, and the rotation speed of the processing surface. In addition, it is also possible not to give the directionality to the second introduction part d2 at all.

In the embodiment shown in FIG. 1, kinds of the fluid to be processed and numbers of the flow path thereof are set two respectively; but they may be one, or three or more. In the embodiment shown in FIG. 1, the second fluid is introduced into between the processing surfaces 1 and 2 from the introduction part d2; but this introduction part may be arranged in the first processing member 10 or in both. Alternatively, a plurality of introduction parts may be arranged relative to one fluid to be processed. The opening for introduction arranged in each processing member is not particularly restricted in its form, size, and number; and these may be changed as appropriate. The opening of the introduction part may be arranged just before the first and second processing surfaces 1 and 2 or in the side of further upstream thereof.

To effect the reaction between the processing surfaces 1 and 2, the second fluid may be introduced through the first introduction part d1 and the first fluid through the second introduction part d2, as opposed to the above description. That is, the expression "first" or "second" for each solvent has a meaning for merely discriminating an $n^{th}$ solvent among a plurality of solvents present, and third or more solvents can also be present.

In the apparatus mentioned above, a reaction such as separation/precipitation and crystallization takes place while effecting forced and uniform mixing between the processing surfaces 1 and 2 which are disposed in a position they are faced with each other so as to be able to approach to and separate from each other, at least one of which rotates relative to the other, as shown in FIG. 1. The particle diameter, the monodispersity, and the solid solution ratio of the solid solution pigment nanoparticles can be controlled by appropriately controlling rotation speed of the processing members 10 and 20, flow rate, distance between the processing surfaces, concentration of raw materials in the fluids to be processed, kind of solvents in the fluids to be processed, and so forth.

Hereunder, the method for producing the solid solution pigment nanoparticle of the present invention will be explained in more detail by showing one example.

At first, from the first introduction part d1, which is one flow path, a fluid which contains the pigment separation solvent as the first fluid is introduced into between the processing surfaces 1 and 2 which are disposed in a position they are faced with each other so as to be able to approach to and separate from each other, at least one of which rotates relative to the other, thereby forming between the processing surfaces a thin film fluid which is constituted of the first fluid.

Then, from the second introduction part d2, which is another flow path, the pigment solution as the second fluid is introduced directly into the thin film fluid formed between the processing surfaces 1 and 2.

By so doing, the first fluid and the second fluid are mixed between the processing surfaces 1 and 2, wherein the distance therebetween is fixed by the pressure balance between the supply pressure of the fluids to be processed and the pressure applied between the rotating processing surfaces, thereby effecting the separation reaction of the nanoparticles; on this occasion, the solid solution pigment nanoparticles formed of two or more different types of pigment can be separated between the processing surfaces 1 and 2 by using as the second fluid a pigment solution having two or more different types of pigment dissolved or molecular-dispersed in a solvent.

In the thin film fluid of the present invention formed between the processing surfaces whose clearance is 1 mm or less, preferably 100 μm or less, or more preferably 50 μm or less, not only prompt and instantaneous mixing and dispersion but also forced molecular dispersion can be effected by rotation of at least one processing member; and thus, further instantaneous mixing/dispersion and crystallization may be possible. In addition, because the fluid flow between the processing surfaces 1 and 2 is a spiral flow from the upstream side to the downstream side of the processing member, an always fresh reaction field is provided continuously in the near part of the opening d20 in the processing surface 2 of the second introduction part d2 through which the second fluid is introduced. As a result, conditions of mixing, stirring, dispersion, reaction, crystallization, and so on can be always kept constant, so that the solid solution pigment nanoparticle always having a constant solid solution ratio can be produced also in the separation of two or more foregoing types of pigment. By so doing, it became possible to obtain the homogeneous solid solution ratio in the solid solution pigment nanoparticles obtained in the present invention.

The solid solution ratio in the solid solution pigment nanoparticles can be readily controlled by changing the introduction rate (ratio such as the weight ratio and the mol ratio) of two or more different types of pigment in the pigment solution to be introduced into between the processing surfaces 1 and 2. To change the introduction rate of two or more different types of pigment in the pigment solution to be introduced into between the processing surfaces 1 and 2, any one of the introduction velocity of the pigment solution into between the processing surfaces 1 and 2 and the pigment concentration in the pigment solution or both may be changed. In the case that a plurality of pigment solutions having two or more types of pigment dissolved in each solvent are introduced into between the processing surfaces 1 and 2, any one of the introduction velocity of at least any one of the pigment solutions into between the processing surfaces 1 and 2 and the pigment concentration in the pigment solution or both may be changed.

For example, in the case that a plurality of the pigment solutions are introduced into between the processing surfaces 1 and 2, a method in which pigment concentration in each pigment solution is kept constant while the introduction velocity of at least any one of the pigment solutions into between the processing surfaces 1 and 2 is changed may be used; or alternatively, in the case that one pigment solution prepared by dissolving two or more types of pigment thereinto is introduced into between the processing surfaces 1 and 2, a method in which the introduction velocity of the pigment solution into between the processing surfaces 1 and 2 is kept constant while the pigment concentration in the pigment solution is changed may be used.

Further, an illustrative example thereof includes a method in which the pigment concentration is changed by diluting the pigment solution just before it is introduced into between the processing surfaces 1 and 2 or just before it is mixed with the pigment separation solvent.

To introduce the pigment solution of two or more different types of pigment into between the processing surfaces 1 and 2 thereby separating the solid solution pigment nanoparticles, as mentioned above, the pigment solution having two or more types of pigment dissolved or molecular dispersed into a solvent may be introduced into between the processing surfaces 1 and 2; or in other embodiment, after a plurality of pigment solutions are prepared by dissolving or molecular dispersing two or more types of pigment into respective solvents thereof, they may be mixed before introduction into between the processing surfaces 1 and 2 such that an intended solid solution ratio may be obtained and then introduced into the processing surfaces 1 and 2; or this plurality of the pigment solutions may be mixed between the processing surfaces 1 and 2.

As mentioned before, the processing apparatus may be provided with, in addition to the first introduction part d1 and the second introduction part d2, the third introduction part d3; and in this case, for example, each of the fluid which contains the pigment separation solvent as the first fluid, the first pigment solution in which at least one type of pigment is dissolved or molecular dispersed in a solvent as the second fluid, and as the third fluid the fluid that contains the second pigment solution in which the pigment different from the at least one type of pigment contained in the first pigment solution is dissolve or molecular dispersed may be introduced separately into the processing apparatus. By so doing, concentration and pressure, introduction velocity, introduction mol ratio of different types of pigment of each fluid can be controlled separately so that the separation reaction of the solid solution pigment nanoparticle, stabilization of particle diameter of the nanoparticles, and the solid solution ratio, which is important in the present invention, may be controlled more precisely. Meanwhile, a combination of the fluids to be processed (first to third fluids) that are introduced into each of the introduction parts may be set arbitrarily. The same is applied if the fourth or more introduction parts are arranged; and by so doing, fluids to be introduced into the processing apparatus may be subdivided.

In addition, temperatures of the fluids to be processed such as the first, the second, and so on may be controlled; and temperature difference among the first fluid, the second fluid, and so on (namely, temperature difference among each of the supplied fluids to be processed) may be controlled either. To control temperature and temperature difference of each of the supplied fluids to be processed, a mechanism with which temperature of each of the fluids to be processed is measured (temperature of the fluid before introduction to the processing apparatus, or in more detail, just before introduction between the processing surfaces 1 and 2) so that each of the fluids to be processed that is introduced into between the processing surfaces 1 and 2 may be heated or cooled may be installed.

In the solid solution pigment nanoparticle obtained by the present invention, the volume-average particle diameter thereof as measured by a particle size distribution measurement instrument (dynamic light scattering method) is 100 nm or less, and the said nanoparticle is neither limited to crystal nor to amorphous; and this can be used naturally in the field of pigment having the object of coloring, as well as in other application such as other functional materials.

EXAMPLES

Hereunder, the present invention will be explained in more detail with referring to Examples; but the present invention is not limited only to these Examples.

Meanwhile, in the following Examples, the term "from the center" means "from the first introduction part d1" of the processing apparatus shown in FIG. 1; the first fluid means the first fluid to be processed which is introduced from the first introduction part d1; and the second fluid means the second fluid to be processed which is introduced from the second introduction part d2 of the processing apparatus shown in FIG. 1.

Examples 1 to 5

In Examples 1 to 5, by using the reaction apparatus in which uniform diffusion, stirring, and mixing are effected in a thin film fluid formed between processing surfaces 1 and 2 which are disposed in a position they are faced with each other so as to be able to approach to and separate from each other, at least one of which rotates relative to the other, as shown in FIG. 1, a pigment solution and a pigment separation solvent are mixed to carry out a separation reaction in this thin film fluid.

A pure water of the pigment separation solvent as the first fluid was introduced from the center with supply pressure of 0.30 MPaG and back pressure of 0.02 MPaG and with rotation speed of 1700 rpm, while, as the second fluid, the pigment solution in which two different types of pigment, of copper phthalocyanine and brominated chlorinated zinc phthalocyanine green, were dissolved in fuming sulfuric acid ($SO_3$ concentration of 30%) was introduced into between the processing surfaces 1 and 2. The first fluid and the second fluid were mixed in the thin film fluid, whereby discharging the solid solution pigment nanoparticles formed of copper phthalocyanine and brominated chlorinated zinc phthalocyanine as a dispersion solution thereof from between the processing surfaces 1 and 2.

To remove impurities from the discharged dispersion solution of the solid solution pigment nanoparticles, the solid solution pigment nanoparticles were loosely aggregated; and then, the aggregated solid solution pigment nanoparticles were collected by filtration, and then washed by pure water to obtain a paste of the solid solution pigment nanoparticles.

A part of the obtained paste of the solid solution pigment nanoparticles was dried at 60° C. under vacuum of −0.01 MPaG to obtain powders of the solid solution pigment nanoparticles. Also, a part of the obtained paste of the solid solution pigment nanoparticles was added by pure water and sodium dodecylsulfate (SDS); and then, the resulting mixture was dispersed by a ultrasonic disperser to obtain a dispersion solution of the solid solution pigment nanoparticles.

Comparative Example 1

As the comparative example, the experiment was done by using a beaker. The pigment solution in which two different types of pigment, copper phthalocyanine and brominated chlorinated zinc phthalocyanine green, were dissolved in fuming sulfuric acid ($SO_3$ concentration of 30%) was charged into pure water in a beaker with stirring.

The solid solution pigment nanoparticles obtained by the Examples and the Comparative Example were subjected to the following analyses.

In the ICP emission spectrometric analysis, concentrations (mol concentrations) of copper (Cu) and zinc (Zn) in the obtained solid solution pigment nanoparticles were measured by using ICPS-8100 (sequential type, manufactured by Shimadzu Corporation).

In the TEM observation and the EDS measurement, JEM-2100 (manufactured by JEOL Ltd.) was used for observation of primary particles of the obtained solid solution pigment nanoparticles and for measurement of concentrations (mol concentrations) of copper (Cu) and zinc (Zn) in the primary particles thereof. These observation and measurement were done as to a plurality of viewing fields to obtain the degree of precision relative to the ratio of the different types of pigment introduced into between the processing surfaces 1 and 2. Meanwhile, the TEM observation and the EDS measurement were done with the condition of 250,000 or more in the observation magnification and in 100 spots for confirmation of the composition ratio to obtain the average value for use.

In measurement of the particle size distribution, by using UPA-UT151 (manufactured by Nikkiso Co., Ltd.), dispersed particle diameters of the solid solution pigment nanoparticles were measured to obtain the volume-average particle diameter for use.

In the spectrum measurement, by using UV-2540 (manufactured by Shimadzu Corporation), the transmission spectra of the dispersion solutions of the solid solution pigment nanoparticles were measured.

Figure 4:
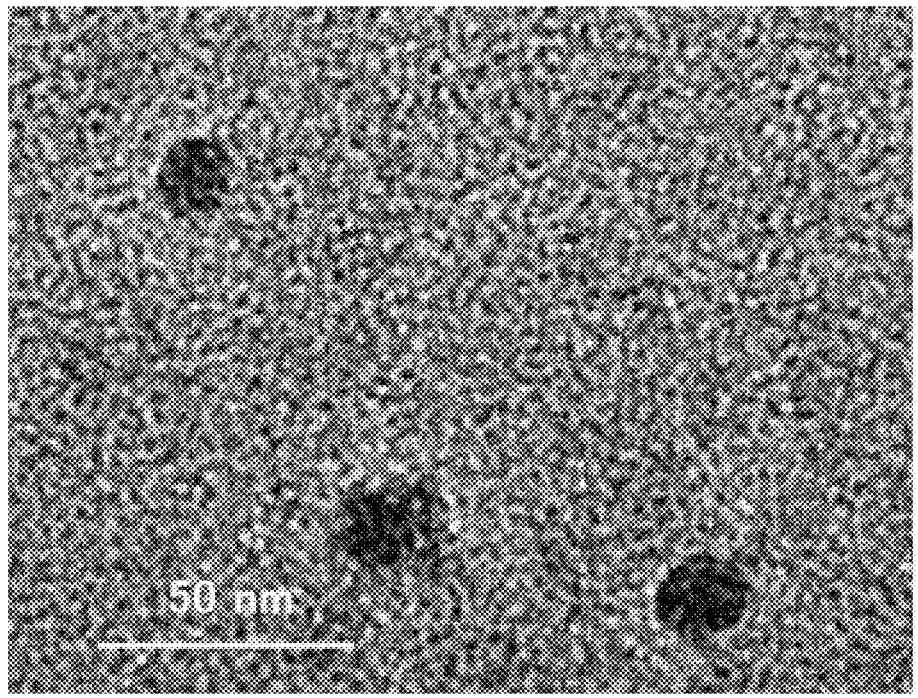
Figure 5:
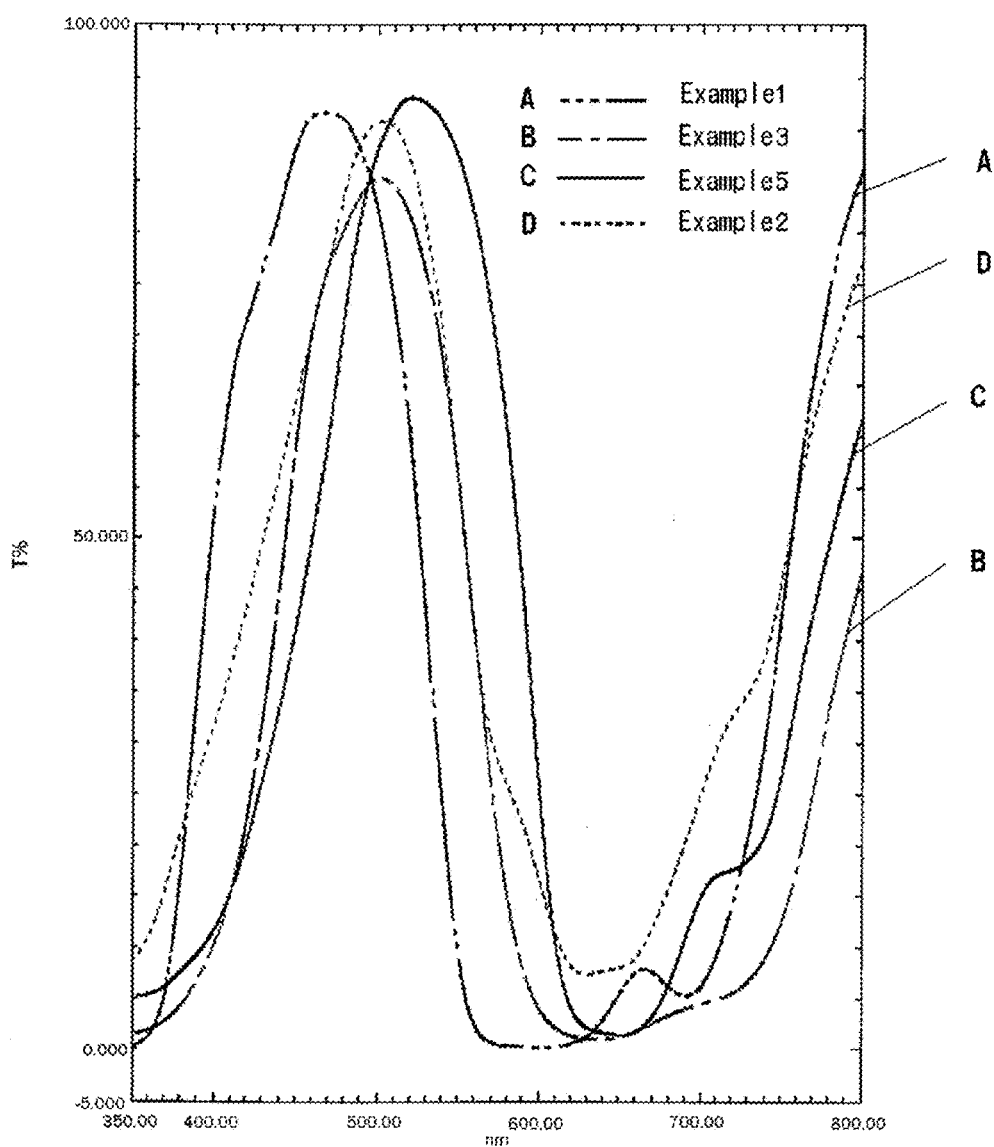

Experiments were carried out by changing the mixture dissolution ratio (mol ratio) of copper phthalocyanine and brominated chlorinated zinc phthalocyanine in the second fluid of fuming sulfuric acid. In Table 1, treatment conditions are shown; and in Table 2, the volume-average particle diameter, the concentration ratios of copper (Cu) and zinc (Zn) measured by the TEM-EDS measurement (shown with the degree of precision) and by the ICP emission spectrometric analysis, and the wavelength (T$\lambda$max) at the maximum transmittance in the transmission spectrum measurement are shown. The supply temperatures of the first fluid and the second fluid shown in Table 1 were measured at where mixing of the first fluid and the second fluid is performed (in other words, just before introduction of the respective fluids into the processing apparatus). In FIG. 4, the TEM picture of the solid solution pigment nanoparticles obtained in Example 3 is shown. In FIG. 5, the transmission spectra in the wavelength region of 350 to 800 nm of each of the dispersion solutions of the solid solution pigment nanoparticle powders obtained in Example 1 (A in FIG. 5), Example 3 (B in FIG. 5), Example 5 (C in FIG. 5), and Comparative Example 2 (D in FIG. 5) which is a mixture of the solid solution pigment nanoparticle powders obtained in Example 1 and Example 5 are shown. Meanwhile, in Comparative Example 2, the mixture dissolution ratio (mol ratio) of copper phthalocyanine and brominated chlorinated zinc phthalocyanine in the second fluid of fuming sulfuric acid shown in Table 1 means the mixing ratio of each of the solid solution pigment nanoparticle powders obtained in Example 1 and Example 5; and the dispersion solution of the solid solution pigment nanoparticles was obtained by using a ultrasonic disperser for the dispersion treatment of a mixture obtained by adding pure water and sodium dodecylsulfate (SDS) into the mixture of the solid solution pigment nanoparticle powders obtained in Example 1 and Example 5.

TABLE 1

| | | First fluid | | Second fluid | | |
| | | | | Mixture dissolution ratio (mol) | | |
| Example | Rotation speed (rpm) | Kind | Temperature (° C.) | Copper phthalocyanine blue | Brominated chlorinated zinc phthalocyanine green | Temperature (° C.) |
|---|---|---|---|---|---|---|
| 1 | 1700 | Pure water | 5 | 1 | 0 | 25 |
| 2 | | | | 5.2 | 1 | |
| 3 | | | | 2.4 | 1 | |
| 4 | | | | 0.4 | 1 | |
| 5 | | | | 0 | 1 | |
| Comparative Example 1 | | Beaker | | 2.4 | 1 | |
| Comparative Example 2 | | Mixture of Example 1 and Example 5 | | 2.4 | 1 | — |

TABLE 2

| Example | Volume-average particle diameter (nm) | Elemental analysis results Element ratio (mol) | | Tλmax (nm) |
|---|---|---|---|---|
| | | TEM-EDS (Cu/Zn) | ICP emission spectrometric analysis (Cu/Zn) | |
| 1 | 10.16 | — (Cu: 100%) | — (Cu: 100%) | 465 |
| 2 | 22.14 | 5.19 ± 5.6% | 5.23 | 471 |
| 3 | 30.12 | 2.42 ± 2.13% | 2.41 | 500 |
| 4 | 9.64 | 0.42 ± 14.2% | 0.42 | 511 |
| 5 | 23.14 | — (Zn: 100%) | — (Zn: 100%) | 520 |
| Comparative Example 1 | 114.23 | 3.97 ± 26.5% | 2.39 | — |
| Comparative Example 2 | 20.56 | | | 504 |

As shown in Table 2, the TEM-EDS measurement results of Examples 2 to 4 were very close to the ICP emission spectrometric analysis results of Examples 2 to 4 as compared with Comparative Example 1. From this, it was found that the solid solution pigment nanoparticles having uniform and homogeneous solid solution ratio could be obtained. In addition, it was found that the solid solution ratio of the solid solution pigment nanoparticles could be controlled by changing the ratio of the different types of pigment to be introduced into between the processing surfaces 1 and 2. From the transmission spectrum measurement results (FIG. 5), it was found that the spectrum characteristics as shown by Tλmax of the solid solution pigment nanoparticles of Example 3 is shifted about 4 nm toward the longer wavelength side as compared with a mixture of the respective single nanopigments in Comparative Example 2 and that shape of the transmission spectrum thereof is different from that of Comparative Example 2, showing that different spectrum characteristics are obtained by forming the uniform solid solution. Presumably this is thought that, although the reason for this is not exactly cleared, because pigment nanoparticles formed of two or more types of pigment are separated as uniform solid solution particles in the thin film fluid, the spectrum characteristics and the color characteristics may be changed due to crystalline state and effects of neighboring molecules and atoms in the solid solution pigment nanoparticles; and thus, even if the same starting materials and the same blending ratios are used as in the cases of Example 3 and Comparative Example 2, the pigment nanoparticles having the uniformly formed solid solution structure are obtained in Example 3 so that various kinds of pigment nanoparticle composition having specific spectrum characteristics and color characteristics can be obtained and that the solid solution pigment nanoparticles which realize diversified color producing properties can be obtained.

Examples 6 to 9

An aqueous sodium sulfide solution ($Na_2S$ aq) with concentration thereof being 9.5% by weight obtained by dissolving sodium sulfide nonahydrate ($Na_2S \cdot 9H_2O$) into pure water was introduced as the first fluid of the pigment separation solvent from the center with supply pressure of 0.50 MPaG and back pressure of 0.10 MPaG and with rotation speed of 1700 rpm, while, as the second fluid, the pigment solution in which two different types of pigment, zinc nitrate hexahydrate ($Zn(NO_3)_2 \cdot 6H_2O$) and manganese nitrate hexahydrate ($Mn(NO_3)_2 \cdot 6H_2O$), were dissolved in pure water was introduced into between the processing surfaces 1 and 2. The first fluid and the second fluid were mixed in the thin film fluid, whereby discharging the solid solution pigment nanoparticles formed of white zinc sulfide (ZnS) pigment and slightly pink manganese sulfide (MnS) pigment as a dispersion solution thereof from between the processing surfaces 1 and 2.

To remove impurities from the discharged dispersion solution of the solid solution pigment nanoparticles, the solid solution pigment nanoparticles were loosely aggregated; and then, the aggregated solid solution pigment nanoparticles were collected by filtration, and then washed by pure water to obtain a paste of the solid solution pigment nanoparticles.

A part of the obtained paste of the solid solution pigment nanoparticles was dried at 60° C. under vacuum of −0.01 MPaG to obtain powders of the solid solution pigment nanoparticles. Also, a part of the obtained paste of the solid solution pigment nanoparticles was added by methanol and a dispersing agent (Thiokalcol 08: manufactured by Kao Corporation); and then, the resulting mixture was dispersed by a ultrasonic disperser to obtain a dispersion solution of the solid solution pigment nanoparticles.

Comparative Example 3

As Comparative Example 3, the experiment was done by using a beaker. The pigment solution in which two different types of pigment, zinc nitrate hexahydrate ($Zn(NO_3)_2 \cdot 6H_2O$) and manganese nitrate hexahydrate ($Mn(NO_3)_2 \cdot 6H_2O$), were dissolved in pure water was charged into pure water in a beaker with stirring.

The ICP emission spectrometric analysis, the TEM observation, and the EDS measurement of the solid solution pigment nanoparticles obtained in the foregoing Examples and Comparative Example were carried out. Meanwhile, the TEM observation and the EDS measurement were done with the condition of 250,000 or more in the observation magnification and in 100 spots for confirmation of the composition ratio to obtain the average value for use.

Figure 6:
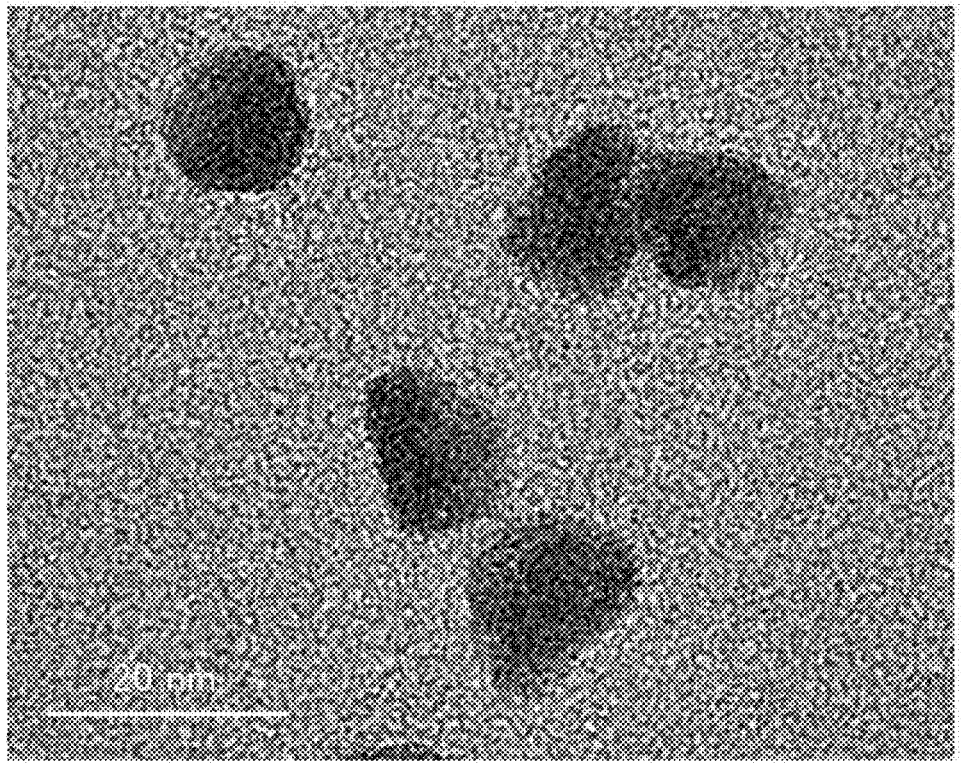

Experiments were carried out by changing the mixture dissolution ratio (mol ratio) of zinc nitrate and manganese nitrate in the second fluid. In Table 3, treatment conditions are shown; and in Table 4, the average particle diameter of 100 particles with magnification of 500,000 by the TEM observation, and the concentration ratios (mol ratio) of zinc (Zn) and manganese (Mn) measured by the TEM-EDS measurement (shown with the degree of precision) and by the ICP emission spectrometric analysis are shown. The supply temperatures of the first fluid and the second fluid shown in Table 3 were measured at where mixing of the first fluid and the second fluid is performed (in other words, just before introduction of the respective fluids into the processing apparatus). In FIG. 6, the TEM picture of the solid solution pigment nanoparticles obtained in Example 8 is shown.

The TEM-EDS measurement results of Examples 7 to 8 were very close to the ICP emission spectrometric analysis results of Examples 7 to 8 as compared with Comparative Example 3. From this, it was found that the solid solution pigment nanoparticles having uniform and homogeneous solid solution ratio could be obtained. In addition, it was found that the solid solution ratio of the solid solution pigment nanoparticles could be controlled by changing the ratio of the different types of pigment to be introduced into between the processing surfaces 1 and 2.

TABLE 3

| | Rotation speed (rpm) | First fluid Kind | First fluid Temperature (° C.) | Second fluid Mixture/Dissolution ratio (mol) Zn(NO$_3$)$_2$·6H$_2$O | Second fluid Mixture/Dissolution ratio (mol) Mn(NO$_3$)$_2$·6H$_2$O | Second fluid Temperature (° C.) |
|---|---|---|---|---|---|---|
| Example 6 | 1700 | Na$_2$S aqueous solution | 20 | 0 | 1 | 20 |
| 7 | | | | 1 | 0.15 | |
| 8 | | | | 1 | 0.05 | |
| 9 | | | | 1 | 0 | |
| Comparative Example 3 | Beaker | | | 1 | 1 | |

TABLE 4

| Example | particle diameter (nm) | Elemental analysis results Element ratio (mol) TEM-EDS (Mn/Zn) | Elemental analysis results Element ratio (mol) ICP emission spectrometric analysis (Mn/Zn) |
|---|---|---|---|
| 6 | 5.64 | — (Mn: 100%) | — (Mn: 100%) |
| 7 | 15 | 0.15 ± 8.61% | 0.15 |
| 8 | 12 | 0.05 ± 19.2% | 0.05 |
| 9 | 4.69 | — (Zn: 100%) | — (Zn: 100%) |
| Comparative Example 3 | 55.61 | 1.56 ± 33.6% | 1.04 |

EXPLANATION OF REFERENCE NUMERALS

1 first processing surface
2 second processing surface
10 first processing member
11 first holder
20 second processing member
21 second holder
d1 first introduction part
d2 second introduction part
d20 opening

The invention claimed is:

1. A method for producing a solid solution pigment nanoparticle, comprising the steps of:
introducing a pigment separation solvent, as a first fluid, with at least one pigment solution having at least two types of pigment dissolved in a solvent, as a second fluid, into a processing device, the processing device comprising at least two processing surfaces facing each other, the at least two processing surfaces being operable to approach to and separate from each other, at least one of the at least two processing surfaces rotating relative to the other;
mixing the first fluid and the second fluid to form a thin film fluid between the at least two processing surfaces; and
separating the solid solution pigment nanoparticle having a controlled solid solution ratio,
wherein the solid solution pigment nanoparticle is produced by separating at least two types of pigment,
wherein the controlled solid solution ratio of at least two types of pigment in a primary particle of the separated solid solution pigment nanoparticle relative to a ratio of at least two types of pigment in the pigment solution mixed with the pigment separation solvent is within 25% as a degree of precision.

2. The method for producing a solid solution pigment nanoparticle according to claim 1, wherein the degree of precision of the solid solution ratio of at least two types of pigment in a primary particle of the separated solid solution pigment nanoparticle relative to the ratio of at least two types of pigment in the pigment solution mixed with the pigment separation solvent is obtained by a TEM-EDS measurement with the observation condition of 250,000 or more magnification.

3. The method for producing a solid solution pigment nanoparticle according to claim 1, wherein the degree of precision of the solid solution ratio obtained by the TEM-EDS measurement relative to the solid solution ratio obtained by an ICP emission spectrometric analysis of the solid solution pigment nanoparticle is within 20%.

4. The method for producing a solid solution pigment nanoparticle according to claim 1, wherein the solid solution ratio of at least two different types of pigment in the solid solution pigment nanoparticle is controlled by controlling a ratio of the at least two different types of pigment in the second fluid to be mixed.

5. The method for producing a solid solution pigment nanoparticle according to claim 4, wherein the ratio of the pigments is a mixture dissolution ratio (mol ratio).

6. The method for producing a solid solution pigment nanoparticle according to claim 1, wherein the controlled solid solution ratio of at least two types of pigment in a primary particle of the separated solid solution pigment nanoparticle relative to a ratio of at least two types of pigment in the pigment solution mixed with the pigment separation solvent is within 10% as a degree of precision.

7. The method for producing a solid solution pigment nanoparticle according to claim 6, wherein the degree of precision of the solid solution ratio of at least two types of pigment in a primary particle of the separated solid solution pigment nanoparticle relative to the ratio of at least two types of pigment in the pigment solution mixed with the pigment separation solvent is obtained by a TEM-EDS measurement with the observation condition of 250,000 or more magnification.

8. The method for producing a solid solution pigment nanoparticle according to claim 6, wherein the degree of precision of the solid solution ratio obtained by the TEM-EDS measurement relative to the solid solution ratio obtained by an ICP emission spectrometric analysis of the solid solution pigment nanoparticle is within 20%.

9. The method for producing a solid solution pigment nanoparticle according to claim 1, wherein the controlled solid solution ratio of at least two types of pigment in a primary particle of the separated solid solution pigment nanoparticle relative to a ratio of at least two types of pigment in the pigment solution mixed with the pigment separation solvent is within 5% as a degree of precision.

10. The method for producing a solid solution pigment nanoparticle according to claim 9, wherein the degree of precision of the solid solution ratio of at least two types of pigment in a primary particle of the separated solid solution pigment nanoparticle relative to the ratio of at least two types of pigment in the pigment solution mixed with the pigment separation solvent is obtained by a TEM-EDS measurement with the observation condition of 250,000 or more magnification.

11. The method for producing a solid solution pigment nanoparticle according to claim 9, wherein the degree of precision of the solid solution ratio obtained by the TEM-EDS measurement relative to the solid solution ratio obtained by an ICP emission spectrometric analysis of the solid solution pigment nanoparticle is within 20%.

12. A method for producing a solid solution pigment nanoparticle, comprising the steps of:
  introducing at least two pigment solutions each having at least one type of pigment dissolved in a solvent, as a first fluid and a second fluid, and a pigment separation solvent, as a third fluid, into a processing device, the processing device comprising at least two processing surfaces facing each other, the at least two processing surfaces being operable to approach to and separate from each other, at least one of the at least two processing surfaces rotating relative to the other, wherein the at least one type of pigment dissolved in the first fluid is different from the at least one type of pigment dissolved in the second fluid;
  mixing the first fluid, the second fluid and the third fluid to form a thin film fluid between the at least two processing surfaces; and
  separating the solid solution pigment nanoparticle having a controlled solid solution ratio,
  wherein the solid solution pigment nanoparticle is produced by separating at least two types of pigment,
  wherein the controlled solid solution ratio of at least two types of pigment in a primary, particle of the separated solid solution pigment nanoparticle relative to a ratio of at least two types of pigment in the pigment solutions mixed with the pigment separation solvent is within 25% as a degree of precision.

13. The method for producing a solid solution pigment nanoparticle according to claim 12, wherein the solid solution ratio of the at least one type of pigment dissolved in the first fluid and the at least one type of pigment dissolved in the second fluid in the solid solution pigment nanoparticle is controlled by controlling a ratio of the at least one type of pigment dissolved in the first fluid and the at least one type of pigment dissolved in the second fluid to be mixed.

14. The method for producing a solid solution pigment nanoparticle according to claim 12, wherein the controlled solid solution ratio of at least two types of pigment in a primary particle of the separated solid solution pigment nanoparticle relative to a ratio of at least two types of pigment in the pigment solutions mixed with the pigment separation solvent is within 10% as a degree of precision.

15. The method for producing a solid solution pigment nanoparticle according to claim 14, wherein the degree of precision of the solid solution ratio of at least two types of pigment in a primary particle of the separated solid solution pigment nanoparticle relative to the ratio of at least two types of pigment in the pigment solutions mixed with the pigment separation solvent is obtained by a TEM-EDS measurement with the observation condition of 250,000 or more magnification.

16. The method for producing a solid solution pigment nanoparticle according to claim 14, wherein the degree of precision of the solid solution ratio obtained by the TEM-EDS measurement relative to the solid solution ratio obtained by an ICP emission spectrometric analysis of the solid solution pigment nanoparticle is within 20%.

17. The method for producing a solid solution pigment nanoparticle according to claim 12, wherein the controlled solid solution ratio of at least two types of pigment in a primary particle of the separated solid solution pigment nanoparticle relative to a ratio of at least two types of pigment in the pigment solutions mixed with the pigment separation solvent is within 5% as a degree of precision.

18. The method for producing a solid solution pigment nanoparticle according to claim 17, wherein the degree of precision of the solid solution ratio of at least two types of pigment in a primary particle of the separated solid solution pigment nanoparticle relative to the ratio of at least two types of pigment in the pigment solutions mixed with the pigment separation solvent is obtained by a TEM-EDS measurement with the observation condition of 250,000 or more magnification.

19. The method for producing a solid solution pigment nanoparticle according to claim 17, wherein the degree of precision of the solid solution ratio obtained by the TEM-EDS measurement relative to the solid solution ratio obtained by an ICP emission spectrometric analysis of the solid solution pigment nanoparticle is within 20%.

20. The method for producing a solid solution pigment nanoparticle according to claim 12, wherein the degree of precision of the solid solution ratio of at least two types of pigment in a primary particle of the separated solid solution pigment nanoparticle relative to the ratio of at least two types of pigment in the pigment solutions mixed with the pigment separation solvent is obtained by a TEM-EDS measurement with the observation condition of 250,000 or more magnification.

21. The method for producing a solid solution pigment nanoparticle according to claim 12, wherein the degree of precision of the solid solution ratio obtained by the TEM-EDS measurement relative to the solid solution ratio obtained by an ICP emission spectrometric analysis of the solid solution pigment nanoparticle is within 20%.

* * * * *